United States Patent [19]

Soreau et al.

[11] 4,191,841

[45] Mar. 4, 1980

[54] PROCESS FOR MANUFACTURING 4-HYDROXY-3,5-DIMETHOXY BENZOIC ACID FROM 3,4,5-TRIMETHOXYBENZOIC ACID

[75] Inventors: Michel Soreau, Montmorency; Yani Christidis, Paris, both of France

[73] Assignee: Societe Francaise Hoechst, Puteaux, France

[21] Appl. No.: 23,376

[22] Filed: Mar. 23, 1979

[30] Foreign Application Priority Data

Apr. 5, 1978 [FR] France .............................. 78 10053

[51] Int. Cl.$^2$ .............................................. C07C 65/04
[52] U.S. Cl. ................................................... 562/475
[58] Field of Search ........................................ 562/475

[56] References Cited

PUBLICATIONS

Steenken, S. et al., Chem. Abst. 86:139056s 1977.
K. Venkateswara Rao et al., Chem. Abst. 16670h 1962.
Kasztreiner, E. et al., Chem. Abstr., vol. 74, 42161m 1971.

Primary Examiner—Paul J. Killos
Attorney, Agent, or Firm—Karl W. Flocks

[57] ABSTRACT

Demethylation of the 3,4,5-trimethoxybenzoic acid is carried out in the presence of an excess of alkali hydroxide in an amount of ethylene glycol just sufficient to obtain a heterogeneous medium sufficiently fluid in the course of the operation. The ethylene glycol monomethyl ether and the water formed are distilled off progressively with their production and the resulting 4-hydroxy-3,5-dimethoxybenzoic acid is separated by acidification by means of a strong acid and crystallization.

5 Claims, No Drawings

PROCESS FOR MANUFACTURING 4-HYDROXY-3,5-DIMETHOXY BENZOIC ACID FROM 3,4,5-TRIMETHOXYBENZOIC ACID

BACKGROUND OF THE INVENTION

1. Field of the Invention

The present invention relates to a process for manufacturing 4-hydroxy-3,5-dimethoxybenzoic acid from 3,4,5-trimethoxybenzoic acid.

2. Description of the Prior Art 4-hydroxy-3,5-dimethoxybenzoic acid or syringic acid is used in the synthesis of various pharmaceutical products. It is generally obtained from 3,4,5-trimethoxybenzoic acid (TMBA) by demethylation of the 4-methoxy group. Two general methods of demethylation of phenolic ethers are known, one in an acid medium, the other in a basic medium.

In the case of TMBA, the demethylation is carried out principally in a concentrated sulphuric acid medium (G. HAHN and H. WASSMUTH, Chem. Ber. 67, 701-2, (1934))-(YOSHISHIGE KATO and MASAICHI YASUE-CA 59 11322f)-(Hungarian Pat. No. 158,280 of 24/01/69—C.A. 74 42161m). The operation is relatively long: 6 to 17 hours and necessitates considerable amounts of acid. The product obtained contains, even after recrystallization, besides a little residual TMBA, dihydroxy-monomethoxy-benzoic acid and a non-negligeable amount of an unidentified impurity. In a hydrochloric medium, under pressure, the yields from the demethylation are low; on the other hand, they are high in 48% hydrobromic acid (C. GRAEBE, E. MARTZ. Ann. Chem. 340, 220-1), but the product obtained is very impure according to the tests carried out and requires several recrystallizations.

Until now, demethylation in a basic medium has not been used to obtain syringic acid from TMBA. In fact, it was known (A. WACEK and H. KESSELRING-Monatshefte. 93. 141-150 (1962)) that TMBA was demethylated practically not at all and distinctly less rapidly than syringic acid in aqueous soda at 100° C. and that, on the other hand, in aqueous or alcoholic soda, under pressure, towards 200° C., the demethylation was accompanied by decarboxylation and that it was not possible to stop at the stage of syringic acid (German Pat. No. 162,658). It is known, in addition, that phenol ethers can be demethylated by heating with soda in ethylene or diethylene glycol (HOUBEN-WEYL vol. 6/3 p. 164). This same method applied to methoxyphenoxy benzoic acids causes, according to the respective positions of the carboxy and methoxy groups, either demethylation, or decarboxylation, or both at the same time (H. E. UNGNADE and L. RUBIN-J. Org. Chem. 16, 1311 and following (1951)). When the —COOH and the —OCH$_3$ are in the para position, as in m-phenoxy, p-methoxy benzoic acid, there is demethylation and decarboxylation at the same time (H. E. UNGNADE and E. F. ORWOLL-J. Am. Chem. Soc. 65, 1736 and following (1948)). With TMBA, using the operational conditions of the literature, this method causes both demethylation and decarboxylation and leads to 2,6-dimethoxy phenol.

GENERAL DESCRIPTION OF THE INVENTION

It has now been found that by heating TMBA in the presence of an alkali hydroxide in excess in an amount of ethylene glycol just sufficient to obtain a heterogeneous medium sufficiently fluid in the course of the operation and by distilling off the monomethyl ether of the ethylene glycol and the water formed progressively with their production, there is obtained in a relatively short time, with good yield, substantially pure syringic acid, notably free from 3-hydroxy 4,5-dimethoxybenzoic acid from dihydroxy monomethoxybenzoic acid. It suffices when no more methyl ether of ethylene glycol is formed to dilute the reaction medium, to acidify it and to crystallize the syringic acid.

The reaction may be represented by the overall equation:

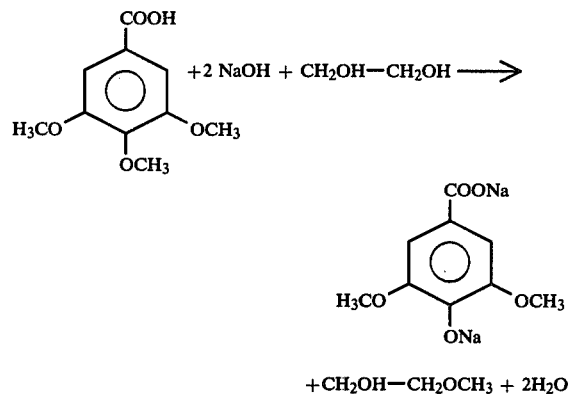

According to the invention, soda or potash may be used as the alkali hydroxide, but soda is preferable, since potash necessitates the use of a larger amount of ethylene glycol to obtain a sufficiently fluid mixture and the double potassium salt of syringic acid is more soluble than the sodium salt, which leads to lower yields. The alkali hydroxide may be used in the form of a concentrated aqueous solution, the water being removed at the start of the reaction by distillation, but it is preferable to use alkali hydroxides in pellets. The molecular ratio of the alkali hydroxide to the TMBA may vary from 2.4 to 4.4; the best yields are obtained with a ratio close to 4; the ratio 3.2 is however most advantageous for economic reasons, an increase in the ratio beyond this value not contributing substantial increases in yield.

The amount of ethylene glycol may be just sufficient to obtain, at the end of the operation, a shakable suspension. With 3.2 moles of soad, a weight of 400 g of ethylene glycol per mole of TMBA is particularly convenient.

The temperature of the reaction medium is adjusted by the distillation of the water and of the monomethyl ether of the glycol; it is close to 160° C. at the start of the distillation and 195° C. at the end of distillation. It may be possible, but this is not indispensable, to maintain the reaction medium at this temperature for a short lapse of time, after the end of the distillation.

The double alkali salt of syringic acid obtained is converted into acid and separated by methods known in themselves. It is, for example, advantageous to dilute the reaction medium after cooling, to acidify it to pH 3 with a strong acid and to allow the syringic acid to crystallize. As strong acid, there may be used, for example, hydrochloric acid or sulphuric acid.

The crude syringic acid thus obtained may be utilized as such; a recrystallization in water however enables the residual TMBA content to be lowered. The process according to the invention enables the production, after recrystallization, of a syringic acid free of 3-hydroxy 4,5-dimethoxybenzoic acid and of dihydroxy monomethoxybenzoic acid and containing less than 1% of TMBA.

Accordingly, as has been indicated above, the syringic acid is useful in the synthesis of pharmaceutical products and notably of a vasopressor medicament.

DESCRIPTION OF PREFERRED EMBODIMENTS

In order that the invention may be more fully understood, some preferred embodiments of practicing the method according to the invention are described below, purely by way of illustrative but non-limiting examples.

EXAMPLE 1

106 g (0.5 mole) of TMBA, 66 g (1.6 mole) of soda in pellets in 200 g of ethylene glycol, are heated under nitrogen. Solution is complete towards 160° C. Distillation commences and stops at the end of 30 minutes, at around 195° C. This temperature is held for 30 minutes. After cooling under nitrogen, it is diluted with 1 l of water and acidified to pH 3 with 170 ml of 10 N sulphuric acid, with heating to bring it to reflux. It is then cooled and left to crystallize for 1 hour. By filtration, 163.3 g of moist, crude product are isolated and this recrystallized in 900 ml of water. After washing and drying, 76.4 g of recrystallized syringic acid are obtained, namely a yield of 77.2% with respect to the TMBA. The acid obtained has a melting point of 210° C. Analysis by liquid-liquid chromatography indicates that it contains less than 1% of residual TMBA and that it is free of 3-hydroxy 4,5-dimethoxybenzoic acid and of dihydroxymonomethoxybenzoic acid.

EXAMPLE 2

Example 1 is reproduced but using 81 g (2.025 moles) of soda in pellets, namely a molecular ratio NaOH/TMBA=4.05 and by acidifying with hydrochloric acid instead of sulphuric acid. The yield is 78.7% of recrystallized product, containing as impurity, only 0.8% of residual TMBA. Five other tests were carried out under the preceding conditions by recycling each time the recrystallization filtrates, introducing them at the end of the reaction into the following operation. The yields were 81.7%-82.6%-79.5%-80.25% and 79%.

EXAMPLE 3

By operating under the same conditions as Example 1 with 97 g (1.6 mole) of potash in pellets, instead of soda, a yield of 54.1% of recrystallized syringic acid was obtained.

EXAMPLE 4—Comparative Test

By way of comparison, a test was carried out with a larger amount of ethylene glycol than that of Example 6. By heating under nitrogen with distillation 212 g (1 mole) of TMBA, 194 g (3 moles) of potash in pellets and 800 ml of ethylene glycol, reaction takes place. The temperature passes from 151° to 190° C. in 1 hour 20; it is held for 2 hours at 190° C. After cooling, dilution with water and neutralization to pH 6, there was obtained, by toluene extraction, 101 g of 2,6-dimethoxy phenol namely a yield of 65.6%. After recrystallization in a water/methanol mixture, with 10% of methanol, the product melted at 54°-55° C. By using a larger amount of ethylene glycol, demethylation and decarboxylation were hence produced.

EXAMPLE 5—Comparative test of demethylation in a sulphuric medium 169.6 g (0.8 mole) of TMBA in 617.5 g (6.3 moles) of 100% sulphuric acid were held for 6 hours at 55° C. It was then run into 3 liters of water, without exceeding 40° C., heated to 95° C. for complete solution, then left to crystallize at 15° C. After filtration, washing and drying, 110.4 g of product were obtained, namely a yield of 69.7% with respect to the TMBA. 25 g recrystallized in 150 ml of water provided 22.7 g of recystallized product (recrystallization yield 90.8%). The yield of recrystallized product was hence 63.3% with respect to the TMBA.

Liquid-liquid chromatographic analysis on the crude and recrystallized products enabled the following impurities to be measured:

|  | Crude Product | Recrystallized Product |
|---|---|---|
| TMBA | 0 | 0.6% |
| 3-hydroxy 4,5-dimethoxy-benzoic acid | 0.3% | 0 |
| Dihydroxy-monomethoxy-benzoic acid | 1.4% | 0.3% |
| Unidentified impurity | 1.9% | 0.9% |

The recrystallized product hence contained dihydroxy monomethoxybenzoic acid and a non-negligeable amount of an unidentified impurity; it was hence less pure than the products obtained by the process according to the invention.

By causing the amount of water used for the crystallization to vary, it was not possible to improve the yields.

A kinetic study of the demethylation carried out in 100% sulphuric acid at 41° C. for 24 hours did not permit a yield of 65% of crude product to be exceeded, titrating less than 90% of syringic acid.

It is self-evident that the present invention has only been described purely by way of explanation and not in any limiting manner and that any useful modification can be introduced therein without departing from its scope as defined by the appended claims.

We claim:

1. Process for manufacturing 4-hydroxy-3,5-dimethoxybenzoic acid by the demethlylation of 3,4,5-trimethoxybenzoic acid, comprising carrying out said demethylation in the presence of an excess of alkali hydroxide in an amount of ethylene glycol just sufficient to obtain a sufficiently fluid heterogeneous medium in the course of the operation, distilling off the ethylene glycol monomethyl ether and the water produced progressively with their formation, separating the resulting 4-hydroxy-3,5-dimethoxybenzoic acid by acidification by means of a strong acid and crystallizing the product.

2. Process according to claim 1, wherein 3.2 to 4.05 moles of alkali hydroxide per mole of 3,4,5-trimethoxybenzoic acid, are used.

3. Process according to claim 2, wherein said alkali hydroxide is caustic soda.

4. Process according to claim 1, wherein 400 g of ethylene glycol are used per mole of 3,4,5-trimethoxybenzoic acid and 3.2 moles of soda.

5. Process for manufacturing 4-hydroxy-3,5-dimethoxybenzoic acid by demethylation of 3,4,5-trimethoxybenzoic acid, comprising carrying out the demethylation in the presence of 3.2 moles of caustic soda per mole of said acid in 400 g of ethylene glycol per mole of said acid, distilling off the ethylene glycol monomethyl ether and water produced progressively with their formation and separating the resulting 4-hydroxy-3,5-dimethoxybenzoic acid by acidification by means of a strong acid of the group constituted by hydrochloric acid and sulphuric acid, and crystallizing in water.

* * * * *